United States Patent [19]

Kohnke

[11] Patent Number: 5,024,653
[45] Date of Patent: Jun. 18, 1991

[54] ASPIRATOR

[75] Inventor: Ole B. Kohnke, Lyngby, Denmark

[73] Assignee: Testa-Laboratorium A/S, Glostrup, Denmark

[21] Appl. No.: 427,943

[22] Filed: Oct. 25, 1989

Related U.S. Application Data

[63] Continuation of Ser. No. 227,457, Aug. 2, 1988, abandoned, which is a continuation of Ser. No. 49,213, May 13, 1987, abandoned.

[30] Foreign Application Priority Data

May 16, 1986 [DK] Denmark ............................ 2314/86

[51] Int. Cl.$^5$ .............................................. A61M 1/00
[52] U.S. Cl. ...................................... 604/35; 604/236; 604/73; 604/216; 604/319
[58] Field of Search .................. 604/35, 30, 216, 217, 604/319, 320, 73–76, 236, 133, 36, 37, 212–213; 417/56

[56] References Cited

U.S. PATENT DOCUMENTS

| | | | |
|---|---|---|---|
| 350,895 | 10/1886 | Ruault | 604/30 |
| 386,603 | 7/1888 | Parsons | 604/30 |
| 657,440 | 9/1900 | McCaw | 604/236 |
| 2,073,069 | 3/1937 | Lee | 604/236 |
| 4,058,123 | 11/1977 | May | 604/35 |
| 4,112,947 | 9/1978 | Nehring | 604/35 |
| 4,319,570 | 3/1982 | Grane | 604/317 |
| 4,457,747 | 7/1984 | Tu | 604/236 |
| 4,460,354 | 7/1984 | Weilbacher et al. | 604/73 |
| 4,462,088 | 2/1987 | Günter | 604/216 |
| 4,643,719 | 2/1987 | Garth et al. | 604/73 |

FOREIGN PATENT DOCUMENTS

| | | | |
|---|---|---|---|
| 0014330 | 5/1929 | Australia | 604/236 |
| 2286657 | 4/1976 | France | 604/236 |
| 1191086 | 11/1985 | U.S.S.R. | 604/319 |

Primary Examiner—C. Fred Rosenbaum
Assistant Examiner—Kathleen A. Daley
Attorney, Agent, or Firm—Watson, Cole, Grindle & Watson

[57] ABSTRACT

An aspirator for removing a body liquid from a body cavity comprising a cylindrical receptacle having a top wall comprising a flap valve, and an aspirating tube, one end of said aspirating tube being connected with the upper part of the receptacle and the other end having such a shape that it can be inserted into the body cavity, said receptacle being partly surrounded by a cylindrical cap-shaped member having a top wall including a flap valve, the cap-shaped member having such a shape that an axial displacement of the cap-shaped member relative to the receptacle produces a vacuum in the space between the cap-shaped member and the receptacle.

The aspirator is more compact and of a simpler construction than the corresponding prior art aspirators.

8 Claims, 2 Drawing Sheets

ASPIRATOR

This application is a continuation of application Ser. No. 227,457, filed Aug. 2, 1988, now abandoned, which in turn is a continuation of application Ser. No. 049,213, filed on May 13, 1987, now abandoned.

BACKGROUND OF THE INVENTION

This invention relates to an aspirator for removing a body fluid from a body cavity, said aspirator comprising a vacuum pump, at least one cooperating receptacle for aspirated fluid and having a one-way valve which closes as the pressure within the vacuum pump exceeds the pressure within the receptacle, and an aspirating tube, one end of said tube communicating with the upper part of the receptacle and the other end having such a shape that it can be inserted into the body cavity.

More particularly, the invention relates to a portable aspirator for use in cases of emergency, e.g. for removing a mixture of mucus and blood from the mouth and/or air passages of an unconscious person.

Aspirators of the above mentioned type typically constitute part of the equipment of ambulances, emergency rescue sets and field hospitals.

A known aspirator of the above mentioned type is described in U.S. Pat. No. 3,084,691. The known aspirator comprises a foot operated pump consisting of a compressible bellows housing a compressible spring adapted to automatically expand the bellows upon removal of the foot. The bellows furthermore comprises a one-way valve for discharge of air during the compression of the bellows and a pipe stub having attached thereto a tube which is connected with a receptacle via a one-way valve which closes as the pressure within the tube increases. The receptacle is connected with an aspirating tube of the type mentioned above.

When using the known aspirator, a vacuum is generated within the bellows during its expansion and the vacuum is transmitted through the receptacle to the aspirating tube through which fluid can be aspirated into the receptacle.

The object of the invention is to provide an aspirator which is more compact and of a simpler construction than the known aspirator discussed above.

SUMMARY OF THE INVENTION

This object is achieved with the aspirator according to the invention, said aspirator being characterized in that the receptacle is at least partially surrounded by a suction device which is displaceable relative to the receptacle and comprises a one-way valve which closes as the pressure in the space between the receptacle and the suction device falls below the ambient pressure.

The aspirator according to the invention is based on the discovery that the vacuum pump and the receptacle can be built together to form a unit in which the exterior side of the receptacle forms part of the vacuum pump.

Obviously, the result is a more compact and simple construction.

The aspirator is particularly advantageous when the receptacle is cylindrical and it is surrounded by a cap-shaped member, and an air-tight annular sealing is provided between the cylindrical receptacle and the cap-shaped member. Such an aspirator is particularly efficient and furthermore it is easy to disassemble, assemble and clean. Thus, such assembly of the aspirator is readily effected by removing the cap-shaed member from the cylindrical receptacle.

The air-tight sealing is preferably located in an annular groove on the exterior side of the cylindrical receptacle.

Alternatively, the suction device may consist of a bellows of an elastic material, e.g. rubber, said bellows being of such a construction that after being stretched, it tends to resume its original shape. The bellows is e.g. connected with the receptacle by means of a releaseable spring means, such that the suction device also in this case can be readily removed in connection with cleaning of the aspirator.

The displacement of the suction device may be effected manually, e.g. by means of a handle but it may also be effected mechanically, e.g. by means of a motor which via a connecting device is connected with a lever mounted in such a manner that it can impart to the suction device a reciprocating movement relative to the receptacle.

A particularly preferred embodiment of the aspirator according to the invention comprises two receptacles located side by side and each comprising a suction pipe connected with the aspirating tube in such a manner that depression of one suction device causes elevation of the other, and vice versa.

Such an aspirator is double acting in that alternating vacuums are generated in the receptacles.

In spite of its small volume, such an aspirator has a high capacity both in case where the movement of the suction devices is effected without auxiliary means, i.e. manually or by foot, and in case it is effected mechanically, e.g. by use of an electric motor.

The aspirator described is particularly suitable for aspirating a mixture of fluid and air from a body cavity because it is suitable both for aspirating accumulations of mucus and for quickly transporting a mixture of fluid and air to the receptacle.

The receptacles for aspirated fluid of the aspirator described above are preferably interconnected so that equalization of the amount of fluid in the two receptacles may take place. This results in a reduced risk of the aspirated fluid contacting the one-way valves of the receptacles.

The receptacle or receptacles of the aspirator of the invention are preferably prepared from a transparent material, e.g. a transparent plastics material. In this manner the user of the aspirator can take steps to make sure that the aspiration is stopped before the receptacle or receptacles are filled with fluid and the valve at the top thereof is contaminated.

When using cylindrical receptacles with a large stroke volume, it is preferable to provide the cap-shaped member with a centrally located guide pin which is displaceably mounted in a centrally located hole provided in the corresponding receptacle. Such a guide arrangement contributes to obtaining an easy and safe movement of the cap-shaped suction device relative to the receptacle.

DESCRIPTION OF THE PREFERRED EMBODIMENT

Figure 1:
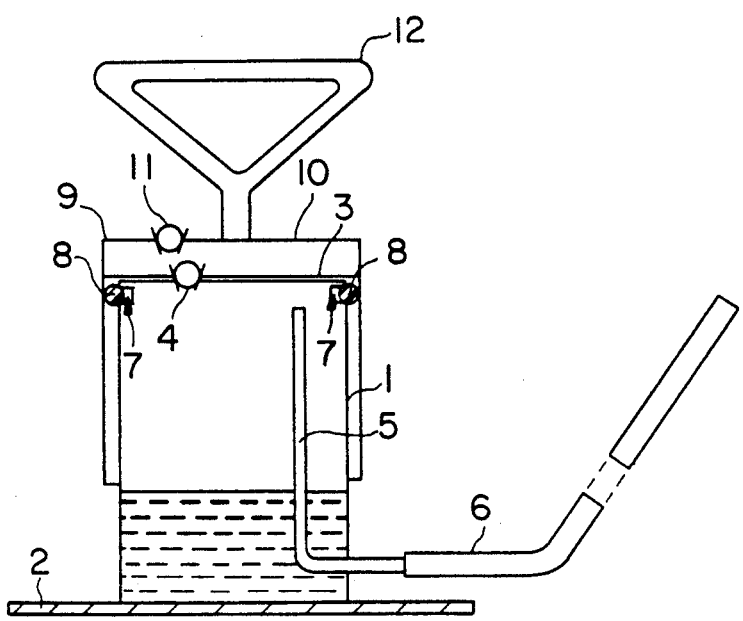
FIG. 1 schematically illustrates a first embodiment of a operated aspirator according to the invention, shown partly in vertical sectional view, FIG. 2 schematically illustrates a further embodiment of a manually operated aspirator according to the invention shown partly in vertical sectional view, FIG. 3 schematically illustrates an embodiment of a mechanically driven aspirator according to the invention shown partly in vertical sectional view, and FIG. 4 schematically illustrates an embodiment of a double acting aspirator according to the invention, shown partly in vertical sectional view.

The aspirator shown in FIG. 1 comprises a cylindrical receptacle mounted on a plate 2. The receptacle 1 comprises a top wall 3 having a one-way valve 4 which closes when the pressure within the receptacle 1 falls to a value which is lower than the pressure above the receptacle 1.

The receptacle 1 furthermore comprises a fluid inlet pipe 5 terminating in the upper part of the receptacle. The opposite end of the pipe 5 is connected with an aspirating tube 6.

At the upper end of the exterior side of the receptacle 1 there is provided an annular groove housing a sealing ring 8 which fits tightly to the interior side of a cylindrical cap-shaped member 9 which is axially displaceable relative to the receptacle 1 and which comprises a top wall 10 in which a one-way valve 11 is located. The valve 11 closes when the pressure in the space between the top wall 3 of the receptacle and the cap-shaped member 9 becomes subatmospheric.

A handle 12 is mounted on the top wall 10.

When the handle 12 is pulled away from the receptacle, a vacuum is generated in the zone between the cap-shaped member 9 and the top wall 3 of the receptacle and this vacuum is transmitted through the valve 4 to the interior of the receptacle 1 and further through the pipe 5 into the aspirating tube 6.

When a pressure is exerted on the top wall 10 and the cap-shaped member 9 is moved downwardly, the one-way valve 4 closes and the one-way valve 11 is opened so as to allow discharge of air.

When the cap-shaped member 9 has reached its bottom position, the aspirator is ready for the commencement of a new suction operation.

Figure 2:
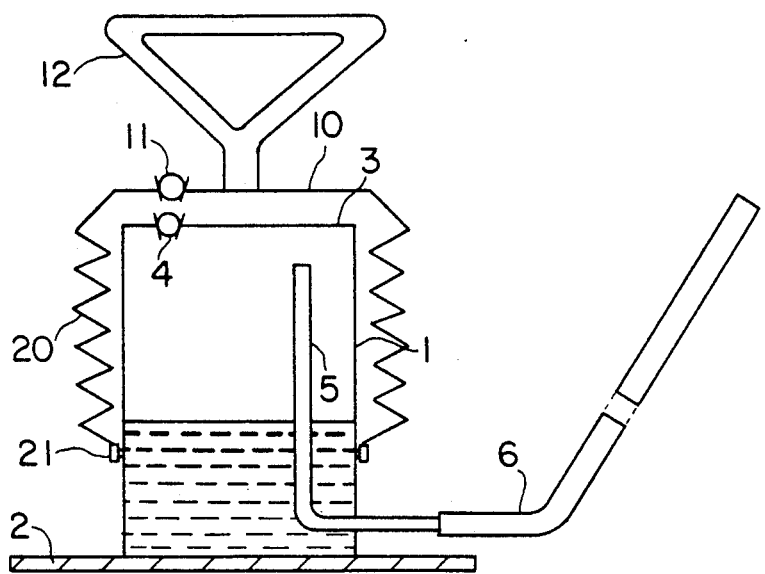

FIG. 2 shows an aspirator which in several respects corresponds to the one shown in FIG. 1 and the same numerals have been used to designate the parts which are common to FIGS. 1 and 2. However, in FIG. 2 the bellows 20 constitutes the cap-shaped member, said bellows being connected with the top wall 10 at its upper end and with the receptacle 1 by means of an annular attachment means 21 at its lower end. The bellows 20 preferably consists of a rubber material which is sufficiently elastic to make the bellows contract automatically after being stretched following the release of the handle attached to the top wall 10.

Figure 3:
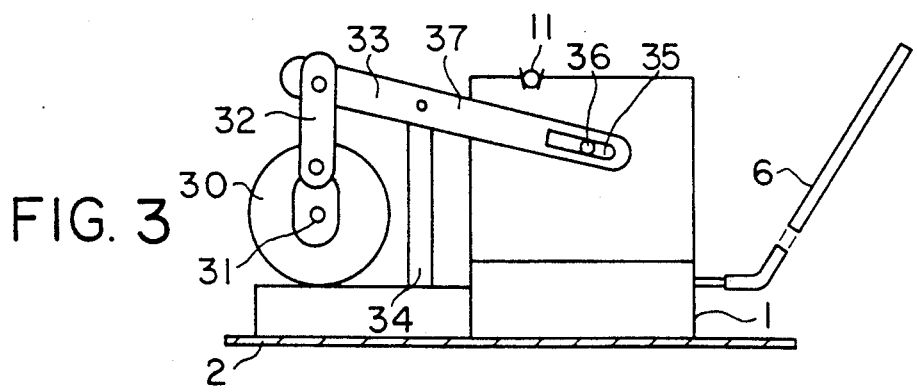

The aspirator shown in FIG. 3 corresponds to the one shown in FIG. 1 with the exeption, however, that the upward and downward movements of the cap-shaped member are effected by means of a motor 30 having a shaft 31 which by means of a connecting piece 32 is connected with one end of a lever 33 mounted in a bearing on a support 37. The other end of the lever 33 has the shape of a fork with two legs, each having an elongated aperture 35 surrounding a pin 36 mounted on the exterior side of the cap-shaped member 9 of the aspirator.

Figure 4:
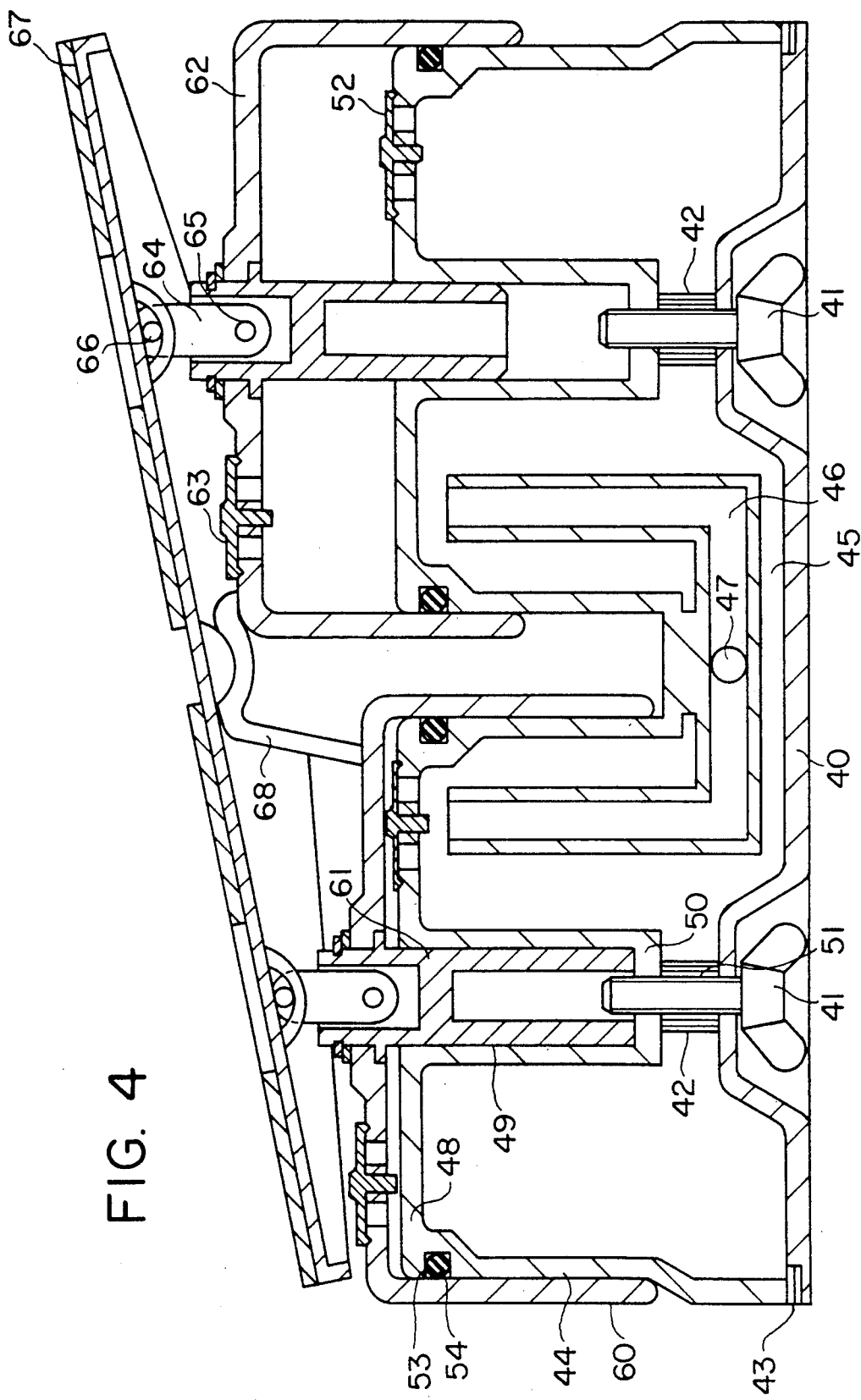

The aspirator shown in FIG. 4 comprises a bottom plate 40. The plate 40 is in air-tight manner and by means of two wing screws and intervening rubber sealings 42 as well as an annular sealing 43 connected with two receptacle upper parts 44 of circular cross section and being interconnected through a passage 45. The two receptacle upper parts 44 are also interconnected through an U-shaped pipe 46 having a central part comprising a pipe stub 47 for attachment of an aspirating tube not shown. Each receptacle part 44 is provided with a top wall 48 comprising an axially extending pipe 49 having a bottom 50 with a hole 51 having an internal thread corresponding to the external thread on the end of the corresponding wing screw 41. The top wall 48 of each receptacle part also comprises a flap valve 52. An annular groove 53 comprising an O-ring 54 is provided at the exterior side of each receptacle part 44 adjacent to the top wall 48. The O-ring 54 is in engagement with the interior side of a cap-shaped cylindrical part 60 having an internal centrally mounted guide pin 61 fitting into the pipe 49 of the corresponding receptacle part 44. Each cap-shaped part 60 comprises a top wall 62 with a flap valve 63. The upper end of each guide pin 61 is hollow and a connecting piece 64 is attached thereto by means of a pin 65. The opposite end of the connecting 64 is connected with a lever 67 by means of a pin 66, and the lever is pivotally mounted in a bearing 68.

In operation the two cap-shaped parts 60 are alternatingly pressed down over the receptacle parts 44. During the upward movement of a cap-shaped part 60 a vacuum is generated in the interior of the aspirator and such vacuum is transmitted through the U-shaped pipe 46 and the pipe stub 47 to the aspirating tube (not shown). As a result thereof liquid is sucked into the aspirating tube and during the continued pumping it passes into the two receptacles in which the liquid is distributed uniformly through the connecting passage 45.

After use, the aspirator is readily disassembled by removing the lever 67 and the cap-shaped parts 60 attached thereto and by unscrewing the wing nuts 41 and removing the bottom plate 40 from the receptacle upper parts 44. After such disassembly it is easy to clean the individual parts and to reassemble them.

I claim:

1. An aspirator for removing a body fluid from a body cavity comprising one receptacle for aspirated fluid, said one receptacle being at least partially surrounded by a reciprocable cap-shaped pump member connected with and capable of generating a vacuum within the one receptacle by displacement of the cap-shaped pump member relative to the one receptacle, the cap-shaped member comprising a one-way valve in communication with the ambient air and which closes when the pressure within the cap-shaped pump member falls below the ambient pressure, the one receptacle comprising a one-way valve in communication with the cap-shaped pump member and which closes when the pressure within the cap-shaped pump member exceeds the pressure within the one receptacle, and an inlet for aspirated liquid provided in the upper part of the one receptacle, said inlet being connected with an aspirating tube having a free end capable of being inserted into a body cavity.

2. An aspirator according to claim 1, wherein the one receptacle is cylindrical and an air-tight annularr sealing being provided between the cylindrical one receptacle and the cap-shaped member.

3. An aspirator according to claim 2, wherein the annular sealing ring is located in an annular groove on the exterior side of the one cylindrical receptacle.

4. An aspirator according to claim 1, wherein the cap-shaped pump member comprises a bellows of an elastic material.

5. An aspirator according claim 1, further comprising a motor for imparting a reciprocating movement to the cap-shaped pump member relative to the one receptacle.

6. An aspirator according to claim 1, further comprising another receptacle placed side-by-side with said one receptacle and in fluid communication therewith, said other receptacle being at least partially surrounded by another respective reciprocable cap-shaped pump member connected with and capable of generating a vacuum within the other receptacle by displacement of the other cap-shaped pump member relative to the other receptacle, the other cap-shaped member comprising a respective one-way valve in communication with the ambient air and which closes when the pressure within the other cap-shaped pump member falls below the ambient pressure, the other receptacle comprising a respective one-way valve in communication with the other cap-shaped pump member and which closes when the pressure within the other cap-shaped pump member exceeds the pressure within the other receptacle, and an inlet for aspirated liquid provided in the upper part of the receptacle, the inlets of each receptacle being connected to a common suction pipe connected with the aspirating tube, and further comprising a lever with two arms, a first arm being connected with the cap-shaped pump member of said one receptacle and a second arm being the other cap-shaped pump member of said other receptacle in such a manner that depression of one of the arms and the respective cap-shaped pump member connected thereto causes elevation of the other of the arms and the respective cap-shaped pump member connected thereto and vice versa.

7. An aspirator according to claim 6, characterized in that the two receptacles are interconnected.

8. An aspirator according to any of claim 6, wherein the cap-shaped pump member on the side facing the corresponding receptacle comprises a guide pin mounted axially displaceable in a hole in the receptacle.

* * * * *